United States Patent [19]

Goebel et al.

[11] Patent Number: 5,525,504
[45] Date of Patent: Jun. 11, 1996

[54] CYTOLYSIN GENE AND GENE PRODUCT

[75] Inventors: Werner Goebel, Veitschochheim, Germany; Stephen J. Libby, San Diego, Calif.; Fred Heffron, Portland, Oreg.

[73] Assignee: Merck Patent Gesellschaft mit beschrankter Haftung, Darmstadt, Germany

[21] Appl. No.: 54,480

[22] Filed: Apr. 30, 1993

[51] Int. Cl.$^6$ ............................ C12N 1/21; C12N 15/31; C12N 15/33; C07K 14/255

[52] U.S. Cl. .................. 435/252.3; 435/252.33; 435/320.1; 514/2; 530/350; 536/23.7; 536/24.32

[58] Field of Search ............................. 435/6, 7.1, 172.3, 435/252.3, 252.33, 320.1; 530/388.4, 835, 350; 536/23.7, 24.32; 514/2

[56] References Cited

PUBLICATIONS

Wahl et. al. 1987, Methods in Enzymology, vol. 152:399–407.
Manietis, et al. 1982, Molecular Cloning: A Laboratory Manual, pp. 324–325, Cold. Spring Harbor.
Young et al. 1983, PNAS, vol. 80:1194–1198.
Gould et al. 1989, PNAS. vol. 86:1934–1938.
Suggs et al. 1981, PNAS. vol. 78:6613–6617.
Gonzalez–Carreo et al. Mol Gen Gen. 1985, 199:106–110.

*Primary Examiner*—Nancy T. Vogel
*Attorney, Agent, or Firm*—Millen, White, Zelano, & Branigan

[57] ABSTRACT

A Salmonella gene, encoding a cytolysin, has been identified by screening for hemolysis on blood agar. The gene (slyA) is present in every strain of Salmonella examined in Shigella, and enteroinvasive *Escherichia coli* (EIEC) but not in other enterobacteriaceae. It is encoded near 28.5 minutes on the chromosome. A SlyA (salmolysin) has hemolytic and cytolytic activity and has a molecular weight predicted by the DNA sequence. $LD_{50}$ and infection kinetics data in mice indicate that the toxin is required for virulence and facilitates Salmonella survival within peritoneal macrophages.

6 Claims, 5 Drawing Sheets

―― OLIGO 1 ――→
ATCGATGCTTTAGTTTTAGCCAAAACTGAAGCTACAGGTGCCAAGTGCGCACTATGTCTGAAAAAATGTCTATTGGTAAGCAAATTTAGCAATACATTTG  100

―― OLIGO 2 ――→
TTTGAGAATACAAATACTGCACACTATTCTAAAATCAGCATAATAACTTAGCAAGCTAATTATAAGGAGATGAAATTGGAATCGCCACTAGGTTCTGAT  200
　　　　　　　　　　　　　　　　　　　　　　　　　　　　　　　　　　　　　　　　 M　K　L　E　S　P　L　G　S　D

CTGGCACGGTTGGTGCGCATTTGGGCGTGCTCTGATTGACCATGCCTCAAGCCTCTGGAATTGACGCAGACACATTGGGTCACGTTGCACAATATCATC  300
 L　A　R　L　V　R　I　W　R　A　L　I　D　H　R　L　K　P　L　E　L　T　Q　T　H　W　V　T　L　H　N　I　H

AATTGCGCCCTGACCAGTCGCCAGATTCAATTGGCTAAAGGCTAAAGGCATTGAGCAGCCATCGCTGGTACGCACGTTGGATCAACTTGAAGATAAGGGCT  400
 Q　L　P　P　D　Q　S　Q　I　Q　L　A　K　A　I　E　Q　P　S　L　V　R　T　L　D　Q　L　E　D　K　G　L

AATTTCGGGCTGGGCAAACTGCGCCAGCTCGTCCGCGATCGTCCGCGAGCCCGAAAAGGGAGCCGATTAAACTGACGGAGCCTGATGGAAGAGGTCATTCAT  500
 I　S　R　Q　T　C　A　S　D　R　R　A　K　R　I　K　L　T　E　K　A　E　P　L　I　A　E　M　E　E　V　I　H

AAAACGCGCGGTGAAATTTGGCTTCTTCAGAGGAGATTGAGCTTCTGATTAAACTTATCGCCAAACTGAACACTATATGGAATTGCACT  600
 K　T　R　G　F　I　L　A　G　I　S　S　E　E　I　F　L　L　I　K　L　I　A　K　L　E　H　N　I　M　E　L　H

CTCACGATTGAGGTGCAGGGGCATACGTGTGACCACTGTGGCCAGTAAAGCCTGGTTTAGCGTGGAGACGGTAACCTGGTGCCGTTGCTGCTGGCCAG  700
 S　H　D　***　　　　　　　　　　　　　　　　　　　　　　　　　　　　　　　　　　　　　←―― OLIGO 3 ――

CACGACACGCTGACCTGCCG  800

FIG. 1

CYTOLYSIN GENE AND GENE PRODUCT

BACKGROUND OF THE INVENTION

Many Gram negative and Gram positive pathogenic microorganisms produce toxins or hemolysins that can lyse eukaryotic cells and contribute to their pathogenicity. S. A. Mims (1982), *The Pathogenesis of Infectious Disease* (Academic Press). The most intensively studied exotoxin produced by Gram negative pathogens are members of the RTX family and are reviewed in A. Ludwig and W. Goebel (1991), Genetic determinants of cytolytic toxins from gram-negative bacteria; in J. E. Alouf and J. H. Freev (eds.), Sourcebook of bacterial proteins, pp. 117–146, Academic Press, London; and in R. A. Welch (1991), *Mol. Micro.* 5, 521–528, and V. Braun et al. (1991), *Critical Reviews in Microbiology* 18, 115–158. The HlyA hemolysin present in strains of uropathogenic *E. Coli* is the best studied of these. HlyA increases *E. Coli* virulence in a rodent model of peritonitis. R. A. Welch et al. (1981), *Nature* 294, 665–667. Although the precise mechanism by which this occurs is unclear, it is suggested that these toxins are involved in attenuating host phagocytic cell function. Welch et al., supra; S. Bhakdi et al. (1986), *Infect. Immun.* 52, 63–69; S. Bhakdi et al. (1990), *J. Clin. Inv.* 85, 1746–1753; S. J. Cavalleri et al. (1984), *Infect. Immun.* 37, 966–974; and B. Konig et al. (1986), *Infect. Immun.* 54, 886–892. Several facultative intracellular pathogens, including rickettsiae, shigellae, *Trypanosoma cruz.*, and *Listeria monocytogenes* share a common trait, i.e., to allow escape from the phagocytic vesicle of professional phagocytic cells. J. W. Moulder (1991), *Micro. Rev.* 55, 143–190; J. Turco et al. (1991), *Infect. Immun.* 59, 1647–1655; B. B. Finlay et al. (1989), *Micro. Rev.* 53, 210–230; and N. W. Andrews et al. (1990), *Cell.* 61, 1277–1287. A defined role in virulence is difficult to assign to most toxins, in part because of the lack of convenient animal models for many organisms. One exception is the listeriolysin made by *Listeria monocytogenes*. The toxin dissolves the phagocytic membrane, allowing the bacteria to escape into the cytoplasm; hemolysin negative mutants are avirulent. J. L. Gaillard et al. (1987), *Infect. Immun.* 55, 1641–1646; S. Kathariou et al. (1987), *J. Bact.* 169, 1291–1297; and D. Portnoy et al. (1989), *Infect. Immun.* 57, 477–486. The infected cell remains intact, and the bacteria are protected from the immune defenses of the host. C. M. Hage-Chahine et al. (1992), *Infect. Immun.* 60, 1415–1421. Transfer of the gene-encoding listeriolysin to the non-pathogenic bacterium *Bacillus subtilis* allows it to also escape the phagosome, suggesting that listeriolysin is both necessary and sufficient for this event. J. Bielecki et al. (1990), *Nature* 345, 175–176.

SUMMARY OF THE INVENTION

The present invention relates to a Salmonella gene (slyA) encoding a cytolysin, or salmolysin, having hemolytic and/or cytolytic activity. The invention also relates to genes encoding a polypeptide having the biological activity of a salmolysin. These genes may be either naturally-occurring, chimeric, gene fragments thereof, or genetically-engineered, e.g., by site-directed mutagenesis, by chemical mutagens, radiation, transposons, or oligonucleotides. DNA and/or RNA sequences which hybridize to the slyA gene or a derivative thereof (e.g., an oligonucleotide of the slyA gene) are also in the scope of the invention. Hybridizing sequences may be selected by their ability to hybridize specifically (e.g., selectively) the salmolysin gene or a fragment thereof under conditions which are generally suitable for selecting DNA sequences (e.g., see *Molecular Cloning*, Sambrook et al., 2nd Ed., 1989, especially 11.45–11.61). The source of DNA sequences capable of hybridizing with the slyA gene or gene fragment may be other bacterial strains, such as disclosed below in FIG. 2, or, e.g., bacillus, aspergillus, amoeba, fungi, yeast, slime mold, insect, bird, mammals, and generally other living organisms and viruses. Although the Salmonella gene isolated herein is used as a representative example, it is recognized that other genes having cytolysin and/or hemolysin activity may be analogously isolated and used as described below. Thus, an aspect of the present invention is a salmolysin gene or salmolysin from any naturally-occurring source.

The present invention also relates to oligonucleotides of the slyA gene or a gene which hybridizes to the slyA gene. The oligonucleotides may contain coding sequences for the slyA gene product or they may contain sequences from non-coding regions of the slyA gene, including, e.g., enhancer, promoter, transcription terminator, and other 5' and 3' sequences from the slyA gene product. The oligonucleotides may be employed, e.g., in the polymerase chain reaction, as probes, and in sequencing (e.g., see Molecular Cloning, Sambrook et al., 2nd Ed. 1989). The oligonucleotides may be used to amplify specific regions of the slyA gene by polymerase chain reaction for the purpose of identifying the presence of bacteria possessing the gene. For example, the presence in body fluids, e.g., blood, serum, saliva, feces, and urine, or in tissues, of strains having the slyA gene may be detected with a slyA probe by hybridization followed by the polymerase chain reaction. Since strains having the slyA gene may be pathogenic to living organisms, the ability to specifically and quickly detect their presence is especially advantageous for diagnostic and treatment purposes. For example, Salmonella, Shigella and EIEC can cause an inflammatory diarrhea. Salmonella more often causes a disseminated infection, while Shigella and EIEC remain within the colonic epithelium, rarely spreading past the lamina propria to produce a disseminated infection.

A slyA gene, gene fragment, or oligonucleotide thereof may be used as a hybridization or amplification probe as conventional in the art, including, in solution, on solid or semi-solid supports, e.g., agarose (Northern or Southern) or polyacrylamide gels, nitrocellulose, nylon, and DEAE-cellulose membranes, microtiter wells, on tissue sections, whole tissue mounts, salivary and chromosome squashes, cells, or by PCR. The methods for hybridization may be performed, e.g., as in *Molecular Cloning*, Sambrook et al., 2nd Ed., 1989. For the purposes of performing PCR, oligonucleotides of a desired length may be selected which are specific for regions of the slyA gene for the purpose of amplifying and detecting the presence of a gene fragment in the sample DNA.

Thus, an aspect of the present invention is also a method of detecting the presence of the slyA gene and e.g. thus the corresponding organisms, preferably Salmonella, Shigella, and enteroinvasive *E. Coli* (EIEC), having the slyA or a related gene, e.g., a gene that cross-hybridizes with the slyA gene. In one embodiment, a nucleic acid specific for the slyA gene is hybridized with a sample containing nucleic acid in which the presence of the organism is to be detected and the presence or absence of binding is determined. The sample may be blood, urine, feces or other body fluids and tissues which contain the organism having the slyA gene. The sample may also be prepared from the latter sources by standard methods of isolating or nucleic acid for test purposes. The method may involve hybridizing and detecting on solid support, e.g., gels and papers, or by PCR. Hybridization may be detected routinely, e.g., by radioactive or enzyme-conjugated or fluorophore-conjugated probes.

This invention is also a method of detecting the presence of the slyA gene, comprising hybridizing two different oligonucleotides according to claim 10 with a nucleic acid containing sample in which the presence of the slyA is to be detected, the conditions of such hybridizing being effective for said specificity of the slyA gene; performing the polymerase chain reaction on the hybridized sample; and detecting the presence or absence of a DNA fragment formed by the polymerase chain reaction. By "conditions of such hybridizing being effective for said specificity of the slyA gene" it meant that hybridization conditions are chosen so that the probe selectively detects a slyA gene in the nucleic acid sample. The selection of such conditions is routinely determined.

The invention also relates to 5' sequences upstream and 3' sequences downstream from the slyA gene. For example, such sequences may be used as heterologous promoters or transcription terminators to control the expression of heterologous genes. Such uses may be accomplished conventionally, (e.g., see *Methods in Enzymology*, Volume 185, Gene Expression Technology, Ed. by D. V. Goeddel, 1990), but substituting the novel sequences of the slyA gene.

The present invention also relates to a slyA gene product, such as salmolysin. The gene product may be prepared according to methods which are conventional in the art, including by transforming microorganisms, e.g., *E. coli*, bacillus, yeast, and aspergillus, with an expression vector comprising the slyA gene. For example, the slyA gene may be placed under control of the T7 promoter in an expression vector. Upon transformation into *E. coli*, large quantities of the protein are produced (see Example 3, below). A salmolysin may also be purified from a natural source by chromatography, e.g., by anion exchange. Thus, another aspect of the invention is an isolated salmolysin. By "isolated", it is meant that the salmolysin is in a form which is not found in nature, preferably at least of a purity where it could be used to elicit antibodies or serve as a vaccine.

Another aspect of the present invention is peptides of a slyA gene product. The peptides may be employed as immunogens for vaccinating organisms susceptible to infection by, e.g., Salmonella, Shigella, and enteroinvasive *Echerichia coli* (EIEC). In addition, the peptides may be used to elicit antibodies to a slyA gene product, e.g., for purposes of detection or in immunoassays. The peptides may also be useful for blocking antibody binding to determine antibody specificity in, e.g., immunoassays and Western blots. These and other immunological techniques are described in e.g., Methods of Enzymology, Volumn 73, ed. by J. Langone and H. Van Vunakis, 1981. Thus, an aspect of the invention is an isolated peptide having a sequence of a salmolysin, e.g, according to FIG. 2, wherein the peptide possesses an activity. The activity may include, e.g., the ability to elicit an immune response, inhibit salmolysin activity or expression, and encode a salmolysin activity.

Antibodies that react with a slyA gene product, or a product of gene capable of hybridizing with the slyA gene, or peptides thereof also relate to the present invention. The antibodies may be naturally-occurring when isolated from an organism which is infected with an organism expressing a slyA or related gene. The antibodies of the present may also be raised to a salmolysin or a peptide thereof. Antibodies in the scope of the invention are monoclonal, polyclonal, fragments thereof, e.g., Fab, (Fab)$_2$, single-chain, chimeric, and genetically-engineered antibodies or peptides capable of reacting with a salmolysin or related gene product. See, e.g., U.S. Pat. Nos. 4,816,567, 5,091,513, 4,444,878, 4,642,334 and 4,978,745.

The peptides and antibodies of this invention may be used in the preparation of diagnostic tests, such as immunoassays. Such diagnostic techniques include, for example, enzyme immune assay (EIA), enzyme multiplied immunoassay technique (EMIT), enzyme-linked immunosorbent assay (ELISA), radioimmune assay (RIA), fluorescence immune assay, either single or double antibody techniques, and other techniques where either the peptides or antibodies of this invention are labeled with some detectable tag. See generally, Enzyme Immunoassay, by Maggio, CRC Press (1981).

A method of detecting salmolysin and/or organisms expressing salmolysin is therefore another aspect of the invention. For example, the method may comprise a method of immunologically detecting salmolysin comprising, reacting a sample in which the presence or absence of salmolysin is to be detected with an antibody specific for the slyA gene product, and detecting the presence or absence of antibody binding. A sample may be a body fluid, urine, feces, or a tissue which has been treated so that it may be used in immunological detection. Another aspect of the invention is an immunoassay for the purpose of detecting slyA in gut, comprising reacting an antibody specific for the slyA gene product and a sample comprising the slyA gene product, and detecting binding of the antibody to the slyA gene product in the sample.

The peptides and antibodies of the present invention may be used as therapeutic formulations, e.g., as vaccines for providing protection against organisms which produce the slyA gene. They may be administered in any conventional dosage formulation, optionally with physiologically acceptable carriers which are generally used in the art.

The present invention is also a kit comprising oligonucleotides which are specific for the salmolysin gene. For example, oligonucleotides, such as oligo 1, oligo 2, or oligo 3, according to FIG. 1, or their complement thereof, may comprise a kit for the purposes of PCR. The kit may be used to detect the presence of organisms which express a slyA gene (for diagnostic purposes.) The kit may include oligonucleotides, buffers, and other reagents used to detect the presence of a nucleic sequence which hybridizes to the oligonucleotides. The oligonucleotides may contain slyA gene product antibodies conjugated fluorophores or enzymes, in which case the kit would include the reagents necessary to detect the fluorophores or enzymes. The kit may also be used in conjunction with a polymerase chain reaction, comprising the reagents to carry out the reaction, including, e.g., oligonucleotide primers to a slyA gene, buffer, DNA polymerase and dNTPs. (See Sambrook et al. supra.)

A. Strains and Media

Wild-type ATCC strain *Salmonella typhimurium* 14028s was used in all virulence studies. Clinical isolates of Salmonella were obtained from the State of California Health Laboratory or the County of San Diego Health Laboratory. Bacteria were cultivated in Luria Bertani medium. Blood agar plates were made in trypticase soy agar (TSA Difco) containing 4% defibrinated sheep red blood cells (Colorado Serum, Denver). Clinical isolates obtained for homology studies included: Yersinia sp., Legionella, Chlamydia, Pasteurella, Acinetobacter, Haemophilus, Proteus, Klebsiella, Neisseria sp., Citrobacter, Campylobacter, Franciscella, Brucella, Listeria, Serupia sp., *E. Coli* K-12, and Aeromonas.

B. Molecular Techniques

A Sau3A partial digest cosmid library of *Salmonella typhimurium* 14028s was constructed in the vector pLARF2 [A. M. Friedman et al. (1982), *Gene*. 18, 289–296] and packaged into lambda particles (Stratagene, La Jolla, Calif.). *E. Coli* LE392 was used as the host for the cosmid library and was plated onto TSA blood plates containing 20 µg/ml tetracycline and incubated for 36 hours at 37° C. to detect zones of hemolysis. A strongly hemolytic colony was chosen for further characterization. Subcloning, sequencing, and Southern analysis were performed by standard techniques [J. Sambrook et al. (1989), *Molecular Cloning: A Laboratory Manual*, Second Edition (Cold Spring Harbor: Cold Spring Laboratory Press)] in either M13 mp19 or pKS (Stratagene, LaJolla, Calif.) using the Sequenase kit (United States Biochemicals). Sequence manipulation and data base searches were performed using IBI MacVector and Gen-Bank.

C. Chromosomal Location of the sly Gene and Southern Hybridizations

A series of "locked-in" Mud-P22 phage insertions at 3-minute overlapping intervals around the *Salmonella typhimurium* chromosome has been created. N. R. Benson et al. (1992), *J. Bact*. 175, 1673–1681, and P. Youderian et al. (1988), *Genetics* 118, 581–592. Each strain packages up to 120 kb (about 3 minutes) of adjacent chromosome when induced with mitomycin C at 1 µg/ml. Phage particles were pelleted from the resulting lysates, and DNA was prepared by phenol extraction. One µg of DNA from each region of the chromosome was immobilized on Nytran using a slot blod apparatus (Schleicher and Schuell) and hybridized with the salmolysin structural PCR amplified gene. All Southern hybridizations were done in 6× SSPE, 10× Denhardts, 0.5% SDS at 65° C. and filters washed in 0.1× SSPE at 65° C. Hybridization, PCR, and other general methods and solutions which are useful in the present invention are described in Sambrook et al., supra.

D. Disruption of the sly Gene

The Sly gene was disrupted by homologous recombination insertion of a suicide vector derived from the RK2 replicon, pFR10. R. C. Roberts et al. (1990), *J. Bact*. 172, 6204–6216. The essential replication gene, trfA, was deleted from this vector and replaced with an internal Ssp1 fragment of slyA. The suicide vector-Sly fragment, pSL2145, was maintained in *E. Coli* S17-1] R. Simon et al. (1983), *Molecular Genetics of Plate-Microbe I Interactions*, A. Puhlar, ed. (St. Paul Minn.: APS Press), pp. 98–106] and transferred to wild-type Salmonella by conjugation. Transconjugates were selected on Brilliant green agar containing sulfadiazine (80 µg/ml) and penicillin (300 µg/ml). Because Salmonella recipient cells lack triA, penicillin resistance can only be stably maintained in recipients by homologous recombination between the internal sly fragment on the suicide plasmid and the sly gene on the chromosome, resulting in sly disruption. Chromosomal DNA was prepared from several penicillin-resistant colonies, restricted with PstI, EcoRV, ClaI, and EcoRV/ClaI, transferred to a membrane, and probed with the $^{32}$P-labelled PCR amplified slyA gene to confirm the interruption of slyA. PCR may be performed as described in Innis et al. (1990), *PCR Protocol: A Guide to Methods and Applications* (Academic Press). All penicillin-resistance colonies examined showed disruption of the slyA gene.

E. Virulence Determination of sly Mutants

Overnight cultures of 14028s (wild type) and SL2161 (slyA–) were grown in LB and LB containing penicillin (200 µg/ml), respectively, and given orally to mice in 200 µl doses with a feeding cannula. Intraperitoneal and intravenous inoculations were given with bacteria washed and diluted in phosphate-buffered saline. $LD_{50}$ values were determined over a four-week period. Course of infection studies were performed by homogenizing tissues in a Stomacher (Tekmar) from infected mice in sterile water, diluting the homogenates in phosphate-buffered saline, and plating or LB agar to determine the number of bacteria per organ.

F. Expression and Partial Purification of a Salmolysin

Methods for the expression of cloned genes in bacteria are well known. To obtain high level expression of a cloned gene in a prokaryotic system, it is often essential to construct expression vectors which contain, at the minimum, a strong promoter to direct mRNA transcription termination. Examples of regulatory regions suitable for this purpose are the promoter and operator region of the *E. coli* β-galactosidase gene, the *E. coli* tryptophan biosynthetic pathway, a T7 or other RNA polymerase promoter or the leftward promoter from the phage lambda. The inclusion of selection markers in DNA vectors transformed in *E. coli* are useful. Examples of such markers include the genes specifying resistance to ampicillin, tetracycline, or chloramphenicol. See Sambrook, supra, for details concerning selection markers and promoters for use in *E. coli*.

The oligonucleotide primers shown in FIG. 1 were used to amplify a 515 bp fragment that contained an NdeI site modified at the start codon and cloned into pRK172 [A. H. Rosenberg et al. (1987), *Gene*. 56, 125–136] at the NdeI site, placing salmolysin expression under the control of the T7 RNA polymerase promoter. The construct, pSL2042, was transformed into *E. Coli* B121 DE3 [F. W. Studier et al. (1990), *Methods in Enzymology* (Academic Press, San Diego), Vol. 185, pp. 6–89] and expression of salmolysin was induced by 1 mM IPTG (isopropylbetagalactoside) in the presence of 200 µg/ml rifamplcin and 50 µCl/ml $^{35}$S-methionine. Proteins were separated by 12% SDS-PAGE, gel stained with Coomassie Brilliant Blue, dried, and exposed to X-ray film. Salmolysin was released from *E. Coli* containing pSL 1117 by the osmotic shock procedure of Neu and Heppel. H. C. Neu et al. (1965), *J. Biol. Chem*. 240, 3685–3692. Proteins were separated by FPLC monoQ anion exchange (Pharmacia) with a 0–1M NaCl gradient, 50 mM Tris-HCl, pH 7.5 and 2 µg/ml of PMSF. Column fractions were assayed for hemolytic activity by adding 50 µl of each fraction to 700 µl of 10% defibrinated, washed sheep erythrocytes and incubated at 37° C. for 1 hour. The amount of released hemoglobin was determined by measuring the optical density of the supernatant at 595 nm. Salmolysin eluted at 150 mM NaCl. Salmolysin could be further purified using preparative isoelectric focusing with a Fletofor (Bio-Rad): all hemolytic activity focused at a pI of 5.5. A hemolytic unit of salmolysin was defined as the amount of partially purified salmolysin required to lyse 50% of a suspension of 10% erythrocytes at 37° C. in 1 hour. One hemolytic unit of salmolysin was heated to 65° C. for 15 minutes, then assayed for activity. EDTA (50 mM final) was added to one hemolytic unit of salmolysin and treated as above. Phospholipase D and cholesterol oxidase activities were assayed by the method described in J. G. Songer et al. (1990), *Infect. Immun*. 58, 131–136.

G. Macrophage Preparation and Infection

Peritoneal macrophages were elicited from Balb/c mice by intraperitoneal injection of proteous peptone, cultured, and infected with wild type and the salmolysin mutant as described in N. A. Buchmeier et al. (1989), *Infect. Immun*. 57, 1–7.

H. General Methods of Molecular Cloning and Genetic Engineering

This invention embraces molecular genetic manipulations that can be achieved in a variety of known ways. The recombinant cells, plasmids, and DNA sequences of the present invention provide a means to produce pharmaceutically useful compounds wherein the compound is a salmolysin.

Generally, the definitions of nomenclature and descriptions of general laboratory procedures used in this application can be found in J. Sambrook et al., *Molecular Cloning, A Laboratory Manual,* (1989) Cold Spring Harbor Laboratory, Cold Spring Harbor, N.Y. The manual is hereinafter referred to as Sambrook and is hereby incorporated by reference. In addition, Ausubel et al., eds., *Current Protocols in Molecular Biology,* (1987 and periodic updates), Greene Publishing Associates, Wiley-Interscience, New York, discloses methods useful in the present application.

All enzymes are used according to the manufacturer's instructions.

Oligonucleotides that are not commercially available can be chemically synthesized according to the solid phase phosphoramidite triester method first described by S. L. Beaucage and M. H. Caruthers, (1981) *Tetrahedron Letts.,* 22(20):1859–1862 using an automated synthesizer, as described in D. R. Needham-VanDevanter et al., (1984) *Nucleic Acids Res.,* 12:6159–6168. Purification of oligonucleotides is by either native acrylamide gel electrophoresis or by anion-exchange HPLC as described in Pearson, J. D., and Regnier, F. E. (1983) *J. Chrom.,* 255:137–149. Nucleotide sizes are given in either kilobases (kb) or base pairs (bp). These are estimates derived from agarose or acrylamide gel electrophoresis or from published DNA sequences.

The sequence of the cloned genes and synthetic oligonucleotides can be verified using the chemical degradation method of Maxam, A. M., et al., (1980) *Methods in Enzymology,* 65:499–560, or similar methods. The sequence can be confirmed after the assembly of the oligonucleotide fragments into the double-stranded DNA sequence using the method of Maxam and Gilbert, supra, or the chain termination method for sequencing double-stranded templates of Wallace, R. B., et al., (1981) *Gene,* 16:21–26. Southern Blot hybridization techniques were carried out according to Southern et al., (1975) *J. Mol. Biol.,* 98:503.

Embodiments of this invention often involve the creation of novel peptides and genes by in vitro mutagenesis. Target genes are isolated in intermediate vectors and cloned for amplification in prokaryotes such as *E. coli,* Bacillus, or Streptomyces. Most preferred is *E. coli* because that organism is easy to culture and more fully understood than other species of prokaryotes. The Sambrook manual contains methodology, e.g., to conduct cloning and genetic engineering methods, *E. coli* strains may be grown in Luria broth (LB) with glucose, or M9 medium supplemented with glucose and acid-hydrolyzed casein amino acids. Strains with resistance to antibiotics were maintained at the drug concentrations described in Sambrook. Transformations may be performed according to the method described by Morrison, D. A. (1977) *J. Bact.,* 132:349–351 or by Clark-Curtiss, J. E., and Curtiss, R. (1983) *Methods in Enzymology,* 101:347–362, Eds. R. Wu et al., Academic Press, New York.

I. Peptides and Antibodies

The peptides can be prepared by conventional processes for synthesizing peptides; more specifically, using processes as described in Schroder and Lubke, *The Peptides,* Vol. 1, published by Academic Press, New York (1966) or Izumiya, et al., *Synthesis of Peptides,* published by Maruzen Publishing Co., Ltd., (1975). For example, an azide process, an acid chloride process, a symmetric anhydride process, a mixed anhydride process, a DCC process, an active ester process (for example: p-nitrophenyl ester, N-hydroxysuccinimide ester, or cyanomethyl ester), a carbodiimidazole process, an oxidative-reductive process, or a DCC/additive process can be used. Solid phase and solution phase syntheses are both applicable to the foregoing processes.

The peptides of the present invention are suitably prepared in accordance with the above processes as typically employed in peptide synthesis, generally either by a so-called stepwise process which comprises condensing an amino acid to the terminal amino acid, one by one in sequence, or by coupling peptide fragments to the terminal amino acid. (Amino groups that are not being used in the coupling reaction must be protected to prevent coupling at an incorrect location.)

In case that a solid phase synthesis is adopted, the C-terminal amino acid is bound to an insoluble carrier or support through its carboxyl group. The insoluble carrier is not particularly limited as long as it has a binding capability to a reactive carboxyl group. Examples of such insoluble carriers include halomethyl resins of polystyrene, such as chloromethyl resins, phenol resins, tert-alkyloxycarbonyl-hydrazidated resins, and the like.

In general, antibodies may be obtained by injecting the desired immunogen or antigen into a wide variety of vertebrates, in accordance with conventional techniques. Suitable vertebrates include mice, rats, rabbits, sheep, and goats, with mice being preferred. Usually, the animals are bled periodically with the successive bleeds having improved titer and specificity. The antigens may be injected intramuscularly, intraperitoneally, subcutaneously, or the like. Chimeric antibodies (mouse human hybrids) made by genetic engineering are also contemplated by this invention.

Polyclonal antibodies are prepared by hyperimmunization of the animal with antigen. Then the blood of the animal is collected shortly after the repeated immunizations and the gamma globulin is isolated. Suitable methods for preparing polyclonal antibodies are described in the *Handbook of Experimental Immunology,* 3d edition, (ed. Weir, 1978).

To obtain monoclonal antibodies, spleen cells from the immunized vertebrate demonstrating the desired antibody response are immortalized. The manner of immortalization is not critical, but the most common method is fusion with a myeloma fusion partner. Other techniques of immortalization include EBV transformation, transformation with bare DNA, such as oncogenes or retroviruses, or any other method which provides for stable maintenance of the cell line and production of monoclonal antibodies. The general process for obtaining monoclonal antibodies is described by Kohler and Milstein, in *Nature,* 256, 495–497 (1975), which is herein incorporated by reference. Human monoclonal antibodies may be obtained by fusion of the spleen cells with an appropriate human fusion partner, such as WI-L2, described in European Application No. 82.301103.6, the relevant portions of which are hereby incorporated by reference. A detailed technique for producing mouse×mouse monoclonal antibodies is taught by Oi and Herzenberg, in *Selected Methods in Cellular Immunology,* 351–372 (eds. Mishell and Shiigi, 1980), which also is herein incorporated by reference. The resulting hybridomas are screened to isolate individual clones, each of which secretes a single antibody species capable of recognizing the antigen.

The peptides and/or antibodies may be used without modification or may be modified in a variety of ways, for example, by labeling. Labeling is intended to mean joining, either covalently or non-covalently, a moiety which directly or indirectly provides for a means of detection. A wide variety of labels are known and include: radionuclides, enzymes, substrates, cofactors, inhibitors, fluorescers, chemiluminescers, magnetic particles and the like.

Many of the techniques for linking the peptides to suitable labels involve the use of their carboxyl groups, through the use of carbodiimide or active esters to form peptide bonds; the formation of sulfides by reaction of a mercapto group with an activated halogen, such as chloromethylstyrene or activated olefin, such as maleimide; formation of a secondary amine by reaction of an amino group with a dialdehyde such as glutaraldehyde, or the like, followed by reduction with sodium cyanoborohydride, or the like.

An amino group-protected amino acid is bound in sequence through condensation of its reactive carboxyl group to the terminal amino group of the growing chain. After synthesizing the complete sequence, the peptide is removed from the insoluble carrier to yield free the peptide. This solid-phase approach is generally described by Merrifield, et al. in *J. Am. Chem. Soc.*, 85, 2149–2156 (1963).

The peptides of this invention can also be prepared through DNA techniques. The amino acid sequence of the desired peptide is used to deduce the codon sequence for the single-stranded DNA, synthesized using conventional synthetic techniques (including multiple gene copy techniques), then the double-stranded DNA is prepared and inserted at a suitable site in a cloning vehicle, vector, or plasmid. An appropriate organism, such as bacteria cells, yeast cells, or mammalian cells, is transformed to obtain expression of the desired peptide.

The prepared peptides of the present invention can be isolated and purified from the reaction mixture by means of peptide separation, for example, by extraction, countercurrent distribution, column chromatography, high performance liquid chromatography, and the like.

BRIEF DESCRIPTION OF THE DRAWINGS

Various other objects, features and attendant advantages of the present invention will be more fully appreciated as the same becomes better understood when considered in conjunction with the accompanying drawings, in which like reference characters designate the same or similar parts throughout the several views.

FIG. 1. Salmolysin Sequence. The sequence of the Sly gene (DNA sequence=SEQ ID NO:1; amino acid sequence= SEQ ID NO:2). The initiation codon is underlined and the termination codon is denoted by *. Sequences surrounded by the two boxes are SspI sites used to construct pSL2145. Primers used for PCR reactions are shown (Oligo 1–3 [SEQ ID NOS:3–5, respectively]).

Figure 2:
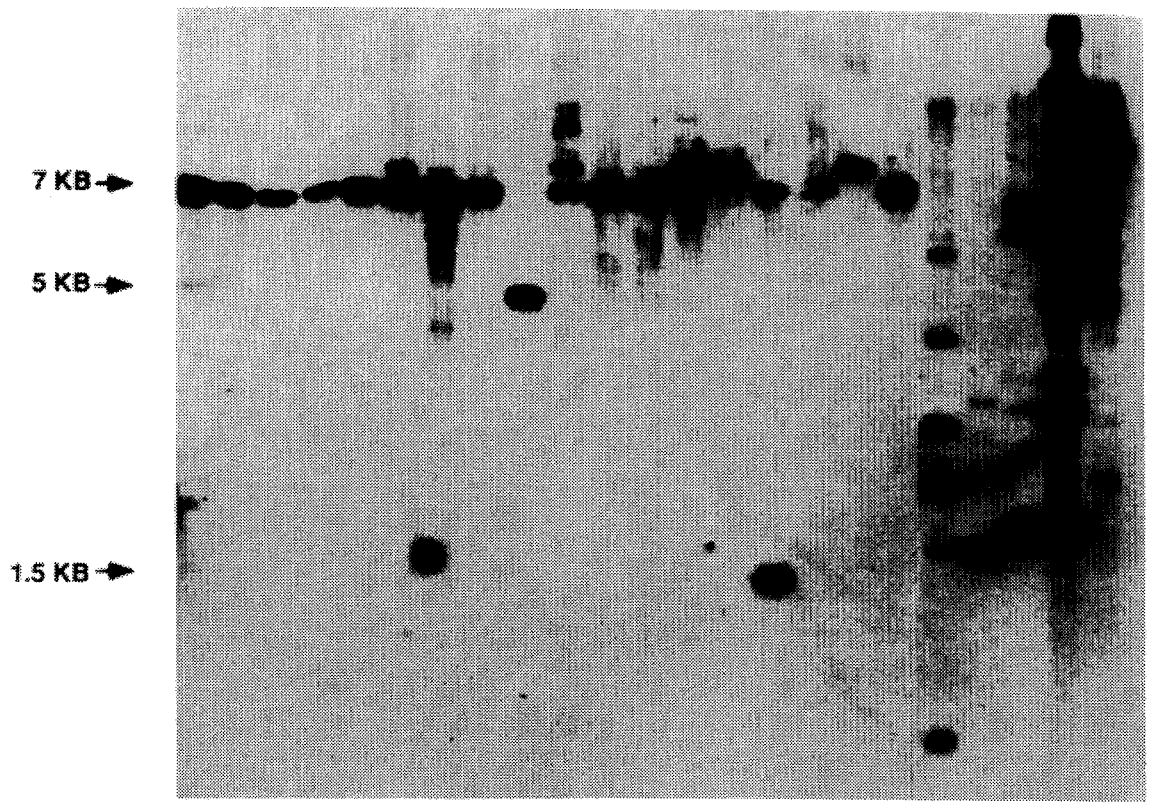
FIG. 2. Conservation of the sly Gene. Chromosomal DNA from clinical isolates of Salmonella was isolated, restricted with PstI transferred to a Nytran, and probed with the labeled PCR amplified slyA fragment. A single 7.0 kb fragment hybridized to the probe with the exception of *S. worthington*, *S. infantis*, and *S. entaritidis*. The slyA gene may be multi-copy in these serotypes. A 6 kb fragment hybridizes with *S. badar*.

In the foregoing and in the following examples, all temperatures are set forth uncorrected in degrees Celsius and unless otherwise indicated, all parts and percentages are by weight.

The entire disclosures of all applications, patents and publications, cited above, are hereby incorporated by reference.

The pre-print entitled "Cytolytic Toxin Encoded by Salmonella is Required for Virulence and Survival within Macrophages" by Stephen J. Libby, Werner Goebel, Albrecht Ludwig, Nancy Buchmeier, Ferric C. Fang, Donald G. Guiney, Frances Bowe, J. Glenn Songer, and Fred Heffron, attached herein as Appendix A, is hereby incorpored by reference.

EXAMPLES

Example 1

Cloning the Salmolysin Gene

Although Salmonella is not usually hemolytic on laboratory culture media, weak zones of hemolysis around some colonies, especially in clinical isolates were occasionally observed. It was suspected that this variable phenomenon might be highly regulated and the putative hemolysin might only be expressed in vivo. Therefore, it was attempted to clone the cognate gene away from its normal regulatory elements. A cosmid clone bank was made from *S. typhimurium* ATCC 14028 in pLAFR2, packaged into bacteriophage lambda in vitro, introduced by infection into *E. coli* strain LE392, and screened for hemolytic activity on blood agar plates. A detailed restriction map of a representative hemolytic clone was prepared and a series of deletions constructed to identify the location of the gene encoding the hemolysin. It was found that a 1.4 kb ClaI/EcoRV fragment (pSL1117) of the original 25 kb cosmid clone was required for hemolotic activity in *E. coli*. The nucleotide sequence of the 1.4 kb fragment was determined and analysis of the sequence adjacent to the CiaI site revealed a 436 base open reading frame that could encode a protein of 16,747 daltons. The polymerase chain reaction (PCR), see, e.g., Innis et al., (1990), was used to amplify a 680 base pair region from chromosomal DNA encompassing the open reading frame. The sequence of this region is shown in FIG. 1. The PCR derived fragment was cloned into pKS (Stratagene, La Jolla, Calif.) and screened for hemolytic activity. This clone, pSL2070, was equally hemolytic as pSL1117, indicating that the 680 base-pair fragment contained all the genetic information necessary for the hemolytic phenotype in *E. coli*. The deduced protein sequence was used to search a translated version of the Genbank DNA database (updated August 1992). The closest matches were compared with slyA using the Fustell protein comparison matrix but no significant short homologies were found. Surprisingly, analysis of the salmolysin coding sequence did not reveal a classical signal sequence. However, it is still possible that salmolysin is exported to the outer membrane or extracellularly in vivo by a sec-independent pathway similar to export of the HlyA [R. A. Welch, *Mol. Micro.* Vol. 5, pp. 521–528 (1991) and Braun, V. & T. Focareta, *Critical Reviews in Microbiology*, Vol. 18, pp. 115–158 (1991)]. Thus, a single gene, which we call slyA for salmolysin, is sufficient to confer hemolytic activity on laboratory strains of *E. coli*.

Example 2

Mapping and Conservation of the Salmolysin Gene in Salmonella sp.

Since the map location for many Salmonella genes have been determined, it was decided to map slyA to determine whether it corresponds to a genetically mapped but unsequenced gene. The precise genetic location of the slyA gene was determined using a modification of the procedure described in [N. R. Benson and B. S. Goldman, *J. Bact.*, Vol. 175, pp. 1673–1681 (1992) and P. Youdenan et al. *Genetics*, Vol. 118, pp. 581–592 (1988)]. Using this procedure, the slyA gene was mapped to a region between 28.5 and 30 minutes. Few genes have been identified in this location, either in Salmonella or in the related region in *E. coli* [F. C. Neidhard, *Escherichia coli* and *Salmonella typhimurium, Cellular and Molecular Biology*, (American Society of Microboloby, Washington, D.C. (1987)].

DNA was extracted from the parent strain, 17 clinical Salmonella isolates, three Shigella serotypes, enteroinvasive *E. coli* (EIEC), and other pathogenic bacteria [ Materials and Methods for list]. Southern hybridization using the 680 bp fragment as a probe showed that the gene is present in all serotypes of Salmonella examined. Shigella and enteroinvasive *E. coli* (EIEC) (FIG. 2) but not in any of the other 25 bacterial species examined (data not shown). A since 7 kb fragment hybridized in most serotypes of Salmonella. Three serotypes showed two fragments that hybridized, suggesting that the slyA gene may be duplicated in some serotypes of Salmonella or there are several PstI sites in or around the slyA gene.

Example 3

Biological Properties of Salmolysin

Figure 3:
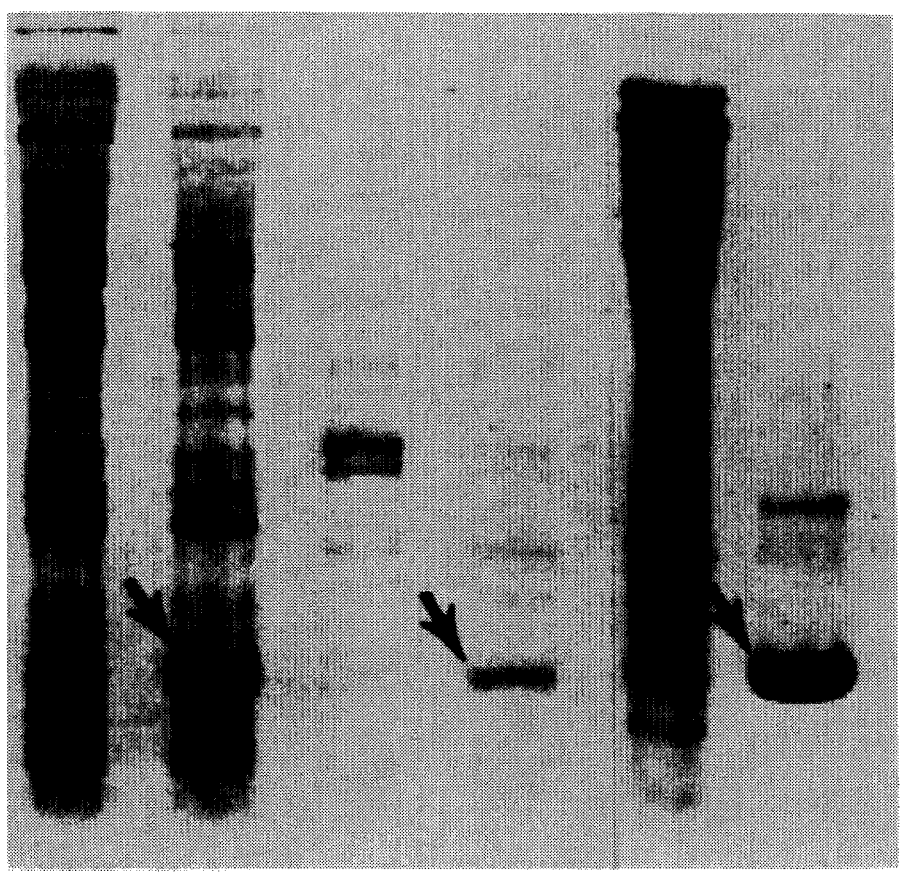
FIG. 3. Size Determination and Partial Purification of Salmolysin. The expression of salmolysin was placed under the control of the inducible T7 RNA polymerase promoter. The oligonucleotide primers show in FIG. 1 were used to amplify a 515 bp Sly containing fragment containing an NdeI site modified at the start codon and cloned into pRK172 in the NdeI site placing salmolysin expression under the control of the T7 RNA polymerase promoter (See Materials and Methods). Lane 1. Total protein from uninduced *E. coli* Bl21 De containing pSL2042 stained with Coomassie Brilliant Blue. Lane 2. Total protein from induced *E. coli* Bl21 De stained with Coomassie Brilliant Blue. The arrow indicates a protein of 16,000 daltons. Lanes 5. and 6. Autoradiograph of Lanes 1 and 2. Lane 3–4. Osmotic shock supernatants from *E. coli* DH5a containing pKS (lane 3) and supernatants from *E. coli* DH5a containing pSL1117 (lane 4) prepared identically and separated by MonoQ anion exchange chromatography with a 0–1M NaCl gradient. A 16,000 dalton protein, indicated by the arrow, was enriched in the 150 mM NaCl containing fraction obtained from cells expressing cloned salmollysin (lane 4). No protein in the corresponding size range was enriched from *E. coli* containing pKS alone.

The size of the sly gene product was determined. SlyA was over-expressed by placing the coding region under the control of T7 RNA polymerase using the PCR primers shown in FIG. 1. A 519 bp fragment was amplified, cloned into pRK172 and transformed into *E. coli* BL21 DE [F. W. Studier et al., *Methods in Enzymology*, Vol. 185, pp. 6–89 (1990)]. Proteins were labeled in the presence of IPTG (which induces expression of T7 RNA polymerase) and $^{35}$S-methionine, then separated by SCS-PAGE. As shown in FIG. 3 (lanes 2 and 6), a single 16,000 dalton protein was specifically labeled. These results are in close agreement with the size of salmolysin predicted from the DNA sequence.

Isolation of functional salmolysin was facilitated by the discovery that the hemolytic activity of the *E. coli* clones expressing the salmolysin gene could be released by osmotic shock. Overnight cultures of *E. coli* expressing cloned salmolysin (pSL1117) were osmotically shocked [F. W. Studier et al., *Methods in Enzymology*, Vol. 185, pp. 6–89 (1990)]. Released salmolysin was partially purified by FPLC MonoQ anion exchange chromatography (Pharmacia); all hemolytic activity eluted at 50 mM NaCl. A 16,000 dalton protein, identical in size to the protein over-expressed under the control of T7 RNA polymerase, was enriched in this fraction (FIG. 3). Identically processed osmotic shock supernatants of *E. coli* with pKS alone had no protein in this size range that eluted at 150 mM NaCl, nor was hemolysin activity detected in any fraction. Salmolysin was found to have an isoelectric point of pI 5.5 determined by preparative isoelectric focusing. Some of the biochemical properties of salmolysin were determined. The hemolytic activity of salmolysin was found to be sensitive to heat (65° C. for 15 minutes) and was fully active in the presence of 50 mM EDTA, unlike the hemolysin from uropathogenic *E. coli* [F. C. Neidhard, *Escherichia coli* and *Salmonella typhimurium, Cellular and Molecular Biology*, (American Society of Microboloby, Washington, D.C. (1987)]. No phospholipase or cholesterol oxidase activity was detected. Salmolysin is also able to lyse nucleated cells as well as a variety of erythrocytes (data not shown). Based on these results, a salmolysin is called a cytolysin.

Example 4

Salmolysin Is Required for Virulence

It was addressed whether salmolysin is required for virulence by comparing a defined slyA *S. typhimurium* mutant with its virulent parental strain in a mouse model of infection. The chromosomal sly gene was disrupted with a RK2-based suicide vector as described in Materials and Methods. An internal fragment of sly was cloned into suicide vector and transferred to *Salmonella typhimurium* 14028s by conjugation and transconjugates selected on penicillin, Brilliant green plates. Southern analysis confirmed the disruption of the sly gene (data not shown). These recombinant colonies contain two partial copies of slyA, neither of which is capable of making an intact copy of salmolysin. The resulting sly mutant is now designated SL2161. Compared with the isogenic wild type parent, SL2161 demonstrated no difference in growth rate, cell or colonial morphology, ability to grow on minimal media containing only salts and glucose (M9 with 0.2% glucose), sensitivity to acid, ability to invade and transcytose epithelial cell monolayers, or the ability to plaque the temperate phage P22 (data not shown).

The $LD_{50}$ values of SL2161 was determined by the oral (i.g.), intraperitoneal (i.p.), and intravenous (i.v.) routes of infection. To carry out $LD_{50}$ experiments, graded does of the parent strain and slyA* derivative (SL2161) were administered to mice and the number of surviving animals recorded after 28 days. The parent 14028s has an $LD_{50}$ of less than 10 organisms when administered i.p. or i.v. and of $6 \times 10^5$ organisms i.g. Table II shows that the $LD_{50}$ of a slyA* derivative is greater than $10^5$ i.p. and greater than $10^9$ when administered orally to mice. This represents a difference of greater than 10,000 fold i.p. and greater than 1000 fold orally. It was also found that the salmolysin mutant is avirulent by intravenous infection at a does of greater than $10^4$ bacteria.

Figure 4B:
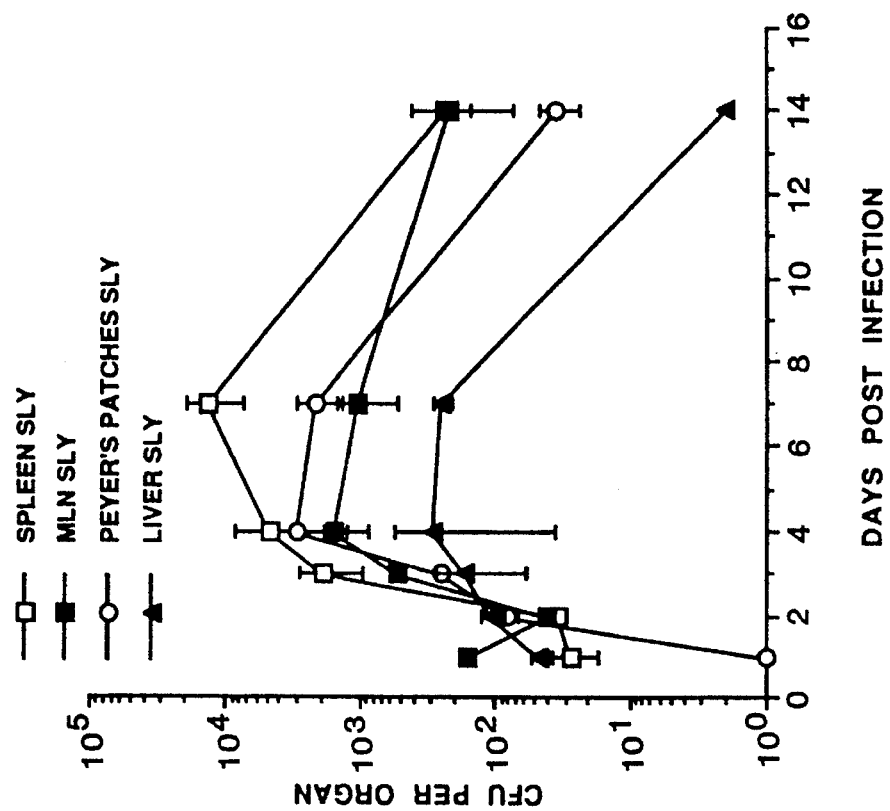
FIGS. 4(A & B). Course of Infection of a Salmolysin Mutant. Oral course of infection. Mice were inoculated orally with $2 \times 10^{10}$ wild type 4028s and SL2161 bacteria. Mice were sacrificed on the days indicated, organs indicated were dissected and homogenized, and the numbers of bacteria in each organ were determined by plating homogenates onto LB agar. This experiment has been repeated several times with the same results.
Figure 4A:
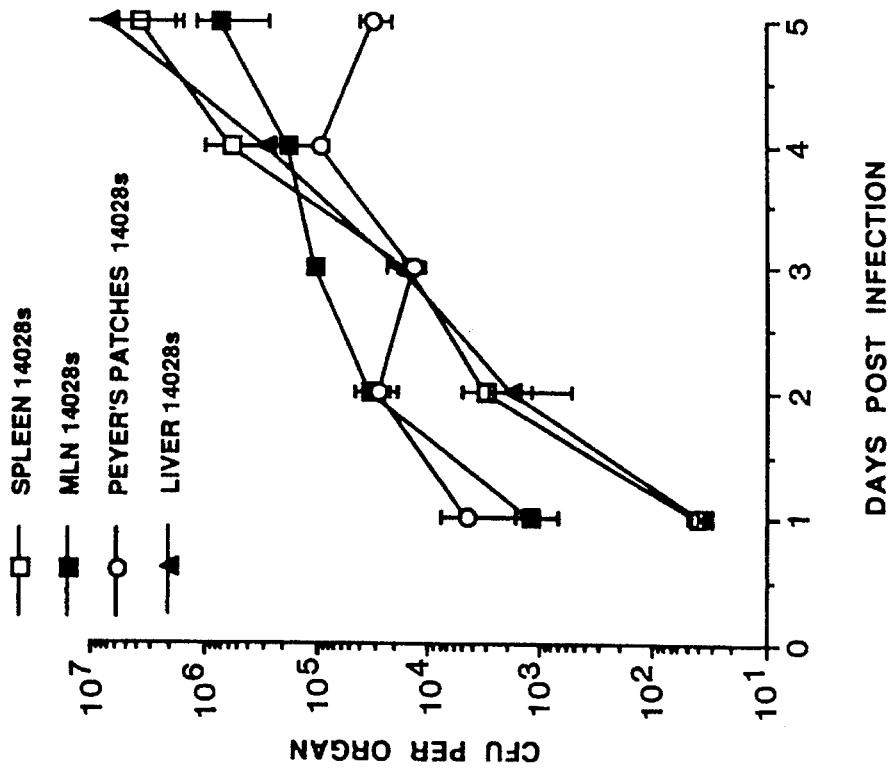
Figure 5:
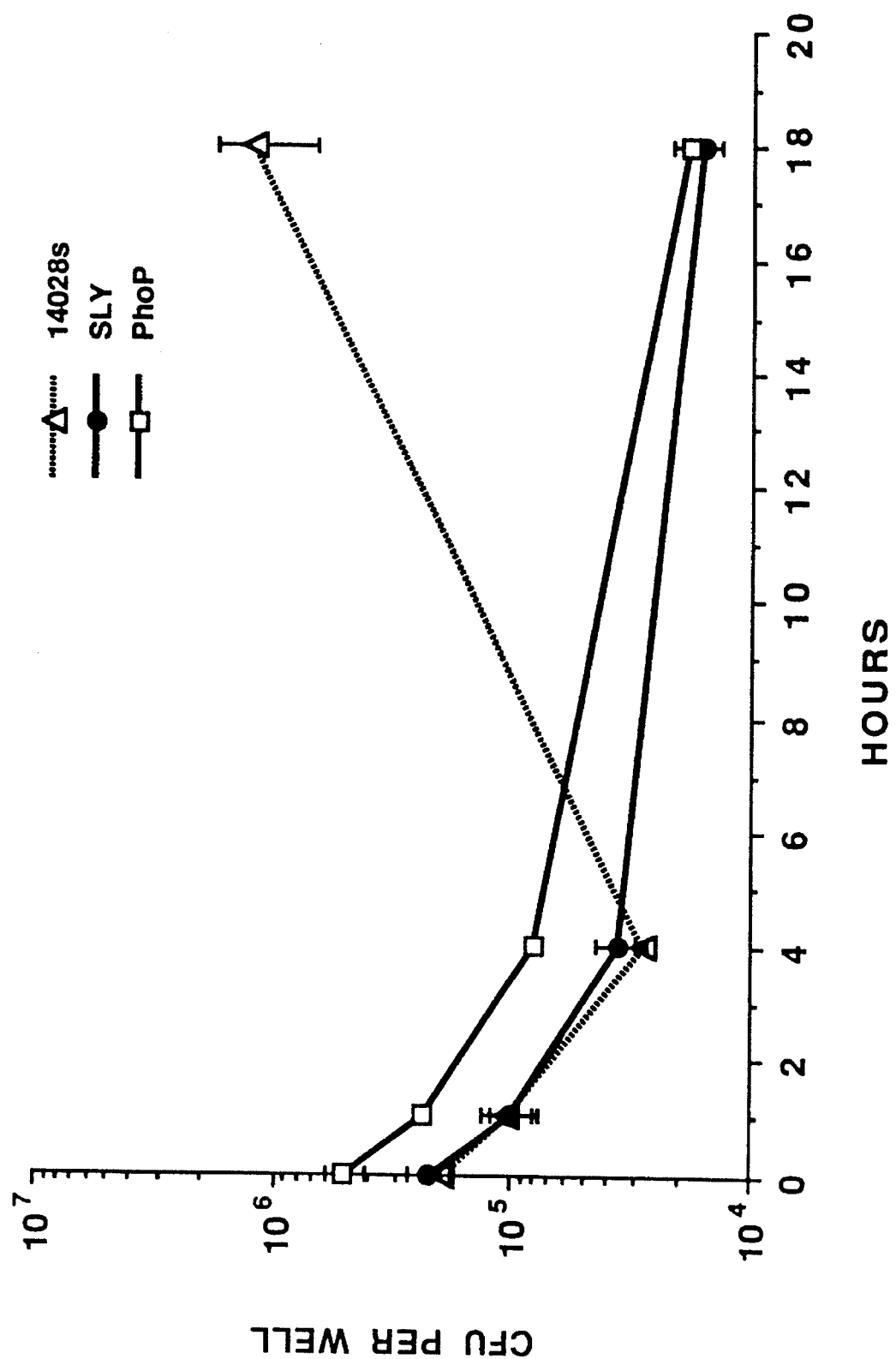
FIG. 5. Macrophage Survival of Salmolysin Mutant. The survival characteristics of the sly mutant strain SL2161 were determined in murine elicits peritoneal macrophages. Wild type 14028s, MS7953(phoP) and SL2161(slyA) were used to infect macrophages. Samples were taken at the times indicated and plated onto LB argar to determine the number of viable bacteria. This experiment was repeated three times, giving nearly identical results.

The in vivo growth kinetics of the mutant were investigated following oral administration to susceptible mice to identify a stage or process in the pathogenesis of the disease in which salmolysin plays a key role. FIGS. 4(A & B) illustrates the dramatically different infection kinetics of the mutant and parent strains. On day zero, about $2 \times 10^{10}$ organisms of either 14028s or its slyA derivative were administered orally (similar results were obtained using a dose of $5 \times 10^8$ bacteria). Within one day, about $10^3$–$10^4$ bacteria of the parent strain were present in the Peyer's patches and mesenteric lymph nodes. Low but significant numbers were present in the liver and spleen. During the next six days exponential growth of the parent was observed in the liver and spleen. By the sixth day there were no surviving animals. In stark contrast to this, rather low numbers of SL2161 reached the mesenteric lymph nodes and Peyer's patches (about 100 versus $10^3$–$10^4$). The liver and spleen were initially invaded by the salmolysin mutant at a somewhat lower level than the parent. The salmolysin mutant grew in these organs for the first three days and was then eliminated very quickly from the liver and somewhat more slowly from the spleen. Similar results were seen following i.v. infection (data not shown). These data demonstrate that the sly lesion is highly attenuating and that the predominant effect is to render the salmolysin mutant vulnerable to some component of the liver and spleen, particularly the liver.

Example 5

Salmolysin Mutants Are Unable to Grown in Murine Macrophages

The survival of mutant and parent within murine macrophages (FIG. 6) was compared. Peritoneal macrophages that had been excited with proteose peptone were used. N. A. Buchmeier et al. (1989), *Infect. Immun.* 57, 1–7; N. Buchmeier et al. (1991), *Infect. Immun.* 59, 2232–2238; and N. Buchmeier et al. (1990), *Science* 248, 730–732. The parent strain is resistant to the bacterial effects of macrophages. As a negative control, a PhoP mutant was used, which is extremely sensitive to these cells. E. A. Groisman et al. (1989), *Proc. Nat. Acad. Sci.* 86, 7077–7082; P. I. Fields et al. (1989), *Science* 243, 1059–1062; and P. I. Fields et al. (1986), *Proc. Nat. Acad. Sci.* 83, 5189–5193. It was found that the sly and phoP mutants were equally sensitive in these assays, suggesting that salmolysin plays a direct role in the survival of Salmonella within macrophages. It was conceivable that the avirulence was not a direct consequence of a mutation in slyA but rather resulted from polar effects of the slyA mutation on another gene located in the same operon as slyA. It was attempted to address this possibility by complementing the slyA mutation with a construct of pACYC184 containing the 680 bl slyA PCR fragment 9pSL2185) in a macrophage survival assay. Complementation with pSL2185 resulted in a ten-fold increase in survival within proteose peptone elicited mouse peritoneal macrophages compared to the isogenic control with the vector alone. Attempts to complement the slyA mutation in vivo in Balb/C mice were unsuccessful due to instability of the plasmid containing the sly gene in vivo.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

TABLE I

Strains and Plasmids

| | Relavent Phenotype | Reference |
|---|---|---|
| Strains | | |
| Salmonella typhimurium | | |
| ATCC 14028s | Mouse Virulent Smooth Strain | 35 |
| SL2161 | slyA::pRR10ΔtrfA Pen$^r$ 14028s | This study |
| MS7953 | phoP 14028s | 35 |
| E. coli Strains | | |
| DH5α | F$^-$ endA hsdR17 ($r_K^-$ $m_K^+$) supE44 thi-1 recA1 gyrA96 φ80lacZ M15 Δ(argF lacZYA) U169 | BRL |
| LE392 | F-hsdR514 ($r_K^-$ $m_K^+$) supE44 supF58 kacY1 or Δ(lacZY)6 galK2 galT22 metB1 trpR55 γ$^-$ | 18 |
| BL21DE | F$^-$ hsdS gal($r_B^-$ $m_B^-$) lacI-lacUV5-gene1 (T7 RNA polymerase lysogenized-expression strain) | 24 |
| S17.1 | Tra$^+$ recA pro thi hsdR chr::RP4-2 | 22 |
| Plasmids | | |
| pKS | Pen$^r$ cloning vector | Stratgene |
| pLAFR2 | Cosmid vector, Tet$^r$ | 18 |
| pACYC184 | Cm$^r$, Tet$^r$ cloning vector | NEB |
| pSL1117 | 1.4 kb ClaI/EcoRV | This study |
| pSL2070 | 680 bp PCR slyA fragment in pKS | This study |
| pSL2042 | 513 bp PCR slyAPCR fragment in pHK172 | This study, 23 |
| pSL2145 | 269 bp internal SspI slyA fragment in pRR10 | This study |
| pSL2185 | 680 bp PCR slyA fragment in pACYC184 in EcoRV site | This study |

TABLE II

Lethal Dose Determination of Salmolysin Mutants

| Bacteria | Dose | Number Surviving |
|---|---|---|
| Intraperitoneal Infection | | |
| 14028s | $1 \times 10^3$ | 0/6 |
| SL2161(sly) | $1 \times 10^3$ | 6/6 |
| SL2161(sly) | $1 \times 10^5$ | 6/6 |
| Oral Infection | | |
| 14028s | $1 \times 10^5$ | 0/6 |
| SL2161(sly) | $1 \times 10^7$ | 6/6 |
| SL2161(sly) | $1 \times 10^9$ | 6/6 |
| Intravenous Infection | | |
| 14028s | $4 \times 10^2$ | 0/4 |

TABLE II-continued

Lethal Dose Determination of Salmolysin Mutants

| Bacteria | Dose | Number Surviving |
|---|---|---|
| SL2161 | $4 \times 10^4$ | 4/4 |

Six week old female BALB/c mice were administered either *S. typhimurium* 14028s (wild type) or SL2161 (salmolysin mutant) as described in Materials and Methods. The number of surviving mice was determined after 21 days. Each experiment was performed twice, giving the identical results. Mice given 14028s intravenously died within 4 days.

SUMMARY

A Salmonella gene, encoding a cytolysin, has been identified by screening for hemolysis on blood agar. DNA sequence analyses together with genetic mapping in Salmonella suggest that it is a previously unreported gene, unrelated to other toxins or hemolysins. The gene (slyA) is present in every strain of Salmonella examined, in Shigella, and enteroinvasive *Escherichia coli* (EIEC) but not in other Enterobacteriaceae. slyA (salmolysin) purified from a derivative of the original clone has hemolytic and cytolytic activity, and has a molecular weight predicted by the DNA sequence. Lethal dose fifty ($LD_{50}$) and infection kinetics in mice suggest that the toxin is required for virulence and facilitates Salmonella survival within mouse peritoneal macrophages.

INTRODUCTION

Many Gram negative and Gram positive pathogenic microorganisms produce toxins or hemolysins that can lyse eukaryotic cells and contribute to their pathogenicity [1]. The most intensively studied exotoxin produced by gram negative pathogens are members of the RTX family and are reviewed in [2, 3] The HlyA hemolysin present in strains of uropathogenic *E. coli* is the best studied of these. HlyA increases *E. coli* virulence in a rodent model of peritonitis [4]. Although the precise mechanism by which this occurs is unclear, it is suggested that these toxins are involved in attenuating host phagocytic cell function [4–8]. Several facultative intracellular pathogens, including rickettsiae, shigellae, *Trypanosoma cruzi*, and *Listeria monocytogenes* share a common trait, i.e. to allow escape from the phagocytic vesicle of professional phagocytic cells [9–12]. A defined role in virulence is difficult to assign to most toxins, in part because of the lack of convenient animal models for many organisms. One exception is the listeriolysin made by *Listeria monocytogenes*. The toxin dissolves the phagocytic membrane, allowing the bacteria to escape into the cytoplasm; hemolysin negative mutants are avirulent [13–15]. The infected cell remains intact and the bacteria are protected from the immune defenses of the host [16]. Transfer of the gene encoding listeriolysin to the non-pathogenic bacterium *Bacillus subtilis* allows it to also escape the phagosome, suggesting that listeriolysin is both necessary and sufficient for this event [ 17].

We have occasionally observed hemolysis by certain Salmonella strains, particularly low passaged clinical isolates. We decided to identify the gene encoding the Salmonella hemolysin and to determine whether it was involved in virulence. We screened a *Salmonella typhimurium* gene bank in *E. coli* for hemolytic activity. Several related clones were identified, of which one was studied in detail. Our results demonstrate that it encodes a cytolysin that is required for virulence in a mouse model of infection.

MATERIALS AND METHODS

Strains and Media

Wild type ATCC strain *Salmonella typhimurium* 14028s was used in all virulence studies. Clinical isolates of Salmonella were obtained from the State of California Health Laboratory or the County of San Diego Health Laboratory. Bacteria were cultivated in Luria Bertani medium. Blood agar plates were made in trypticase soy agar (TSA Difco) containing 4% defibrinated sheep red blood cells (Colorado Serum, Denver). Clinical isolates obtained for homology studies included: Yersinia sp., Legionella, Chlamydia, Pasteurella, Acinetobacter, Haemophilus, Proteus, Klebsiella, Neisseria sp., Citrobacter, Campylobacter, Franciscella, Brucella, Listeria, Serupla sp., Serrtia, *E. coli* K-12, and Aeromonas Molecular Techniques A Sau3A partial digest cosmid library of *Salmonella typhimurium* 14028s was constructed in the vector pLARF2 [18] and packaged into lambda particles (Stratagene, Calif.). *E. coli* LE392 was used as the host for the cosmid library and was plated onto TSA blood plates containing 201 µg/ml tetracycline and incubated for 38 hours at 37° C. to detect zones of hemolysis. A strongly hemolytic colony was chosen for further characterization. Subcloning, sequencing and Southern analysis were performed by standard techniques [19] in either M13 mp19 or pKS (Stratagene, LaJolla Calif.) using the Sequenase kit (United States Biochemicals). Sequence manipulation and data base searches were done using IBI MacVector and GenBank (update 71 August 1992).

Chromosomal Location of the sly Gene and Southern Hybridizations

A series of "locked in" Mud-P22 phage insertions at 3 minute overlapping intervals around the *Salmonella typhimurium* chromosome has been created [20,28]. Each strain packages up to 120 kb (about 3 minutes) of adjacent chromosome when induced with mitomyicin C at 1 µg/ml. Phage particles were pelleted from the resulting lysates and DNA was prepared by phenol extraction. One µg of DNA from each region of the chromosome was immobilized on Nytran using a slot blot apparatus (Schleicher and Schuell) and hybridized with the salmolysin structural PCR amplified gene. All Southern hybridizations were done in 6× SSPE, 10× Denhardts, 0.5% SDS at 65° C. and filters washed in 0.1× SSPE at 65° C.

Disruption of the sly Gene

The sly gene was disrupted by homologous recombination insertion of a suicide vector derived from the RK2 replicon, pRR10 [21]. The essential replication gene trfA was deleted from this vector and replaced with an internal Sspl fragment of slyA. The suicide vector-sly fragment, pSL2145, was maintained in *E. coli* S17-1 [22] and transferred to wild type Salmonella by conjugation. Transconjugates were selected on Brilliant green agar containing sulfadiazine (80 µg/ml) and penicillin (300 µg/ml). Because Salmonella recipient cells lack trfA, penicillin resistance can only be stable maintained in recipients by homologous recombination between the internal sly fragment on the suicide plasmid and the sly gene on the chromosome, resulting in sly disruption. Chromosomal DNA was prepared from several penicillin resistant colonies, restricted with Pstl, EcoRV, Clal, and EcoRV/Clal, transferred to a membrane, and probed with the $^{32}$P-labled PCR amplified slyA gene to confirm the interruption of slyA. All penicillin resistant colonies examined showed disruption of the slyA gene.

Virulence Determination of sly Mutants

Overnight cultures of 14028s (wild type) and SL2161 (slyA−) were grown in LB and LB containing penicillin (200 μg/ml) respectively and given orally to mice in 200 μl doses with a feeding cannula. Intraperitoneal and intravenous inoculations were given with bacteria washed and diluted in phosphate buffered saline. $LD_{50}$ values were determined over a 4 week period. Course of infection studies were performed by homogenizing tissues in a Stomacher (Tekmar, Colo.) from infected mice in sterile water, diluting the homogenates in phosphate buffered saline, and plating on LB agar to determine the number of bacteria per organ.

Partial Purification of Salmolysin and T7-directed Synthesis

The oligonucleotide primers shown in FIG. 1 were used to amplify a 515 bp fragment that contained an NdeI site modified at the start codon and cloned into pRK 172 [23] at the NdeI site, placing salmolysin expression under the control of the T7 RNA polymerase promoter. This construct, pSL2042, was transformed into E. coli Bl21 DE3 [24] and expression of salmolysin was induced by 1 mM IPTG (isopropylbetagalactoside) in the presence of 200 μg/ml rifampicin, and 50 μCi/ml $^{35}$S-methionine. Proteins were separated by 12% SDS-PAGE, gels stained with Coomassie Brilliant Blue, dried, and exposed to X-ray film. Salmolysin was released from E. coli containing pSL1117 by the osmotic shock procedure of Nu and Heppel [25]. Proteins were separated by FPLC MonoQ anion exchange (Pharmacia) with a 0–1M NaCl gradient, 50 mMTris-HCl, pH 7.5 and 2 μg/ml of PMSF. Column fractions were assayed for hemolytic activity by adding 50 μl of each fraction to 700 μl of 10% defibrinated, washed sheep erythrocytes and incubated at 37° C. for one hour. The amount of released hemoglobin was determined by measuring the optical density of the supernatant at 595 nm. Salmolysin eluted at 150 mM NaCl. Salmolysin could be further purified using preparative isoelectric focusing with a Rotofor (BioRad): all hemolytic activity focused at a pI of 5.5. A hemolytic unit of salmolysin was defined as the amount of partially purified salmolysin required to lyse 50% of a suspension of 10% erythrocytes at 37° C. in one hour. One hemolytic unit of salmolysin was heated to 65° C. for 15 minutes then assayed for activity. EDTA (50 mM final) was added to one hemolytic unit of salmolysin and treated as above. Phospholipase D and cholesterol oxidase activities were assayed by the method described in [26].

Macrophage Preparation and Infection

Peritoneal macrophages were elicited from Balb/c mice by intraperitoneal injection of proteous peptone, cultured, and infected with wild type and the salmolysin mutant as described in [27].

RESULTS

Cloning the Salmolysin Gene

Although Salmonella is not usually hemolytic on laboratory culture media, we had occasionally observed weak zones of hemolysis around some colonies, especially in clinical isolates. We suspected that this variable phenomenon might be highly regulated and the putative hemolysin might only be expressed in vivo. We therefore attempted to clone the cognate gene away from its normal regulatory elements. A cosmid clone bank was made from S. typhimurium ATCC 14028 in pLAFR2, packaged into bacteriophage lambda in vitro, introduced by infection into E. coli strain LE392, and screened for hemolytic activity on blood agar plates. A detailed restriction map of a representative hemolytic clone was prepared and a series of deletions constructed to identify the location of the gene encoding the hemolysin. We found that a 1.4 kb ClaI/EcoRV fragment (pSL1117) of the original 25 kb cosmid clone was required for hemolytic activity in E. coli. We determined the nucleotide sequence of the 1.4 kb fragment and analysis of the sequence adjacent to the ClaI site revealed a 436 base open reading frame that could encode a protein of 16,747 daltons. The polymerase chain reaction (PCR) was used to amplify a 680 base pair region from chromosomal DNA encompassing the open reading frame. The sequence of this region is shown in FIG. 1 (DNA sequence=SEQ ID NO:1; amino acid sequence=SEQ ID NO:2). The PCR derived fragment was cloned into pKS (Stratagene, La Jolla, Calif.) and screened for hemolytic activity. This clone, pSL2070, was equally hemolytic as pSL1117, indicating that the 680 base-pair fragment contained all the genetic information necessary for the hemolytic phenotype in E. coli. The deduced protein sequence was used to search a translated version of the Genbank DNA database (updated August 1992). The closest matches were compared with slyA using the Pustell protein comparison matrix but no significant short homologies were found. Surprisingly, analysis of the salmolysin coding sequence did not reveal a classical signal sequence. However, it is still possible that salmolysin is exported to the outer membrane or extracellularly in vivo by a sec-independent pathway similar to export of the HlyA [2, 3]. Thus, a single gene, which we call slyA for salmolysin, is sufficient to confer hemolytic activity on laboratory strains of E. coli.

Mapping and Conservation of the Salmolysin Gene in Salmonella sp.

Since the map location for many Salmonella genes have been determined, we decided to map slyA to determine whether it corresponds to a genetically mapped but unsequenced gene. The precise genetic location of the slyA gene was determined using a modification of the procedure described in [20, 28] (see Materials and Methods). Using this procedure, we mapped the slyA gene to a region between 28.5 and 30 minutes. Few genes have been identified in this location, either in Salmonella or in the related region in E. coli [29].

DNA was extracted from the parent strain, 17 clinical Salmonella isolates, three Shigella serotypes, enteroinvasive E. coli (EIEC), and other pathogenic bacteria (see Materials and Methods for list). Southern hybridization using the 680 bp fragment as a probe showed that the gene is present in all serotypes of Salmonella examined, Shigella, and enteroinvasive E. coli (EIEC) (FIG. 2) but not in any of the other 25 bacterial species examined (data not shown). A single 7 kb fragment hybridized in most serotypes of Salmonella. Three serotypes showed two fragments that hybridized, suggesting that the slyA gene may be duplicated in some serotypes of Salmonella or there are several PstI sites in or around the slyA gene. Preliminary experiments suggests that the slyA cognates in Shigella and EIEC are on extra chromosomal plasmids (data not shown). What role a related gene in Shigella and enteroinvasive E. coli may play in virulence, if at all, in these organisms is currently unknown.

Biological Properties of Salmolysin

The size of the sly gene product was determined. slyA was over-expressed by placing the coding region under the control of T7 RNA polymerase using the PCR primers shown in FIG. 1 (Oligos 1–3=SEQ ID NOS:3–5, respectively). A 519 bp fragment was amplified, cloned into pRK 172 and transformed into *E. coli* BL21 DE [24]. Proteins were labeled in the presence of IPTG (which induces expression of T7 RNA polymerase) and $^{35}$S-methionine, then separated by SDS-PAGE. As shown in FIG. 3 (lanes 2 and 6), a single 16,000 dalton protein was specifically labeled. These results are in close agreement with the size of salmolysin predicted from the DNA sequence.

Isolation of functional salmolysin was facilitated by the discovery that the hemolytic activity of the *E. coli* clones expressing the salmolysin gene could be released by osmotic shock. Overnight cultures of *E. coli* expressing cloned salmolysin (pSL1117) were osmotically shocked [24]. Released salmolysin was partially purified by FPLC MonoQ anion exchange chromatography (Pharmacia); all hemolytic activity eluted at 150 mM NaCl. A 16,000 dalton protein, identical in size to the protein over-expressed under the control of T7 RNA polymerase, was enriched in this fraction (FIG. 3). Identically processed osmotic shock supernatants of *E. coli* with pKS alone had no protein in this size range that eluted at 150 mM NaCl, nor was hemolysin activity detected in any fraction. Salmolysin was found to have an isoelectric point of pI 5.5 determined by preparative isoelectric focusing. Some of the biochemical properties of salmolysin were determined. The hemolytic activity of salmolysin was found to be sensitive to heat (65° C. for 15 minutes) and was fully active in the presence of 50 mM EDTA, unlike the hemolysin from uropathogenic *E. coli* [29]. No phospholipase or cholesterol oxidase activity was detected. We have preliminary evidence that salmolysin is able to lyse nucleated cells as well as a variety of erythrocytes (data not shown). Based on these results, we have called salmolysin a cytolysin.

Salmolysin Is Required for Virulence

We have addressed this crucial question by comparing a defined slyA− *S. typhimurium* mutant with its virulent parental strain in a mouse model of infection, The chromosomal sly gene was disrupted with a RK2-based suicide vector as described in Materials and Methods. An internal fragment of sly was cloned into suicide vector and transferred to *Salmonella typhimurium* 14028s by conjugation and transconjugates selected on penicillin, Brilliant green plates. Southern analysis confirmed the disruption of the sly gene (data not shown). These recombinant colonies contain two partial copies of slyA, neither of which is capable of making an intact copy of salmolysin. The resulting sly mutant is now designated SL2161. Compared with the isogenic wild type parent, SL2161 demonstrated no difference in growth rate, cell or colonial morphology, ability to grow on minimal media containing only salts and glucose (M9 with 0.2% glucose), sensitivity to acid, ability to invade and transcytose epithelial cell monolayers, or the ability to plaque the temperate phage P22 (data not shown).

We first determined the $LD_{50}$ values of SL2161 by the oral (i.g.), intraperitoneal (i.p.), and intravenous (i.v.) routes of infection. To carry out $LD_{50}$ experiments, graded doses of the parent strain and slyA− derivative (SL2161) were administered to mice and the number of surviving animals recorded after 28 days. The parent 14028s has an $LD_{50}$ of less than 10 organisms when administered i.p. or i.v. and of 6×10$^5$ organisms i.g. Table II shows that the $LD_{50}$ of a slyA− derivative is greater than 10$^5$ i.p. and greater than 10$^9$ when administered orally to mice. This represents a difference of greater than 10,000 fold i.p. and greater than 1000 fold orally. We have also found that the salmolysin mutant is avirulent by intravenous infection at a dose of greater than 10$^4$ bacteria.

The in vivo growth kinetics of the mutant were investigated following oral administration to susceptible mice to identify a stage or process in the pathogenesis of the disease in which salmolysin plays a key role. FIG. 4 illustrates the dramatically different infection kinetics of the mutant and parent strains. On day zero, about 2×10$^{10}$ organisms of either 14028s or its slyA derivative were administered orally (similar results were obtained using a dose of 5×10$^8$ bacteria). Within one day, about 10$^3$–10$^4$ bacteria of the parent strain were present in the Peyer's patches and mesenteric lymph nodes. Low but significant numbers were present in the liver and spleen. During the next six days exponential growth of the parent was observed in the liver and spleen. By the sixth day there were no surviving animals. In stark contrast to this, rather low numbers of SL2161 reached the mesenteric lymph nodes and Peyer's patches (about 100 versus 10$^3$–10$^4$). The liver and spleen were initially invaded by the salmolysin mutant at a somewhat lower level than the parent. The salmolysin mutant grew in these organs for the first three days and was then eliminated very quickly from the liver and somewhat more slowly from the spleen. Similar results were seen following i.v. infection (data not shown). These data demonstrate that the sly lesion is highly attenuating and that the predominant effect is to render the salmolysin mutant vulnerable to some component of the liver and spleen, particularly the liver.

Salmolysin Mutants Are Unable to Grow in Murine Macrophages

Our final experiment was to compare survival of mutant and parent within murine macrophages (FIG. 6). We used peritoneal macrophages that had been elicited with proteose peptone [27, 31, 32]. The parent strain is resistant to the bactericidal effects of macrophages. As a negative control we used a phoP mutant which is extremely sensitive to these cells [33–35]. We found that the sly and phoP mutants were equally sensitive in these assays, suggesting that salmolysin plays a direct role in the survival of Salmonella within macrophages. It was conceivable that the avirulence was not a direct consequence of a mutation in slyA but rather resulted from polar effects of the slyA mutation on another gene located in the same operon as slyA. We have attempted to address this possibility by complementing the slyA mutation with a construct of pACYC184 containing the 680 bp slyA PCR fragment (pSL2185) in a macrophage survival assay using peritoneal macrophages. Complementation with pSL2185 resulted in a ten-fold increase in survival within proteose peptone elicited mouse peritoneal macrophages compared to the isogenic control with the vector alone. Attempts to complement the sly A mutation in vivo in Balb/C mice were unsuccessful due to instability of the plasmid containing the sly gene in vivo.

DISCUSSION

We have identified an essential virulence factor in Salmonella. A cytolytic toxin, encoded near 28.5 minutes on the chromosome, is required for survival within peritoneal macrophages and for virulence in a mouse infection model. The toxin, which we call salmolysin, does not have any significant homology to other genes in Genbank, nor does it contain any readily identifiable motifs such as the RTX motif found in the *E. coli* hemolysin [2]. SlyA appears to be present in all Salmonella, Shigella, and EIEC strains examined, but not in many other bacteria tested. By these criteria, salmolysin may define a new family of cytolysins.

It is surprising that Salmonella strains are not obviously hemolytic on blood agar given that they encode this potent cytolysin. One explanation for this comes from studies in progress, aimed at understanding its regulation. A transcriptional fusion of slyA to lacZ results in constitutive expression of lacZ in *E. coli* just as we observe hemolytic activity in *E. coli*. However, lacZ was not expressed in *Salmonella typhimurium* from the same transcriptional fusion. This suggests that salmolysin is expressed only under specific environmental conditions in Salmonella, although we have been unable to precisely identify them. Using the same fusion we also found that expression of sly is independent of phoP/phoQ, a major intracellular regulator and katF, the starvation regulator [36, 37] The fact that a slyA cognate is found in Shigella and EIEC suggests that these bacteria may share a similar virulence mechanism, perhaps related to survival within macrophages. We are currently analyzing the slyA cognates in Shigella and EIEC.

Given that salmolysin probably acts on the eukaryotic cell membranes, it is curious that it does not contain a signal sequence for its export. However, signal sequence independent protein export has been demonstrated for other hemolysins such as HlyA of uropathogenic *E. coli*. In this case, the transport signal appears to be located at its carboxy rather than amino terminal end. HlyA requires the products of hlyB and D together with the chromosomal encoded tolC for its export. Salmolysin does, however, contain a significant hydrophobic region at its carboxy terminal end (AA 115-133) which may form a membrane spanning α-helix. The question of whether this sequence could be involved in secretion or in pore formation in the target cell membrane has not been addressed experimentally as yet.

Salmolysin Salmonella mutants are blocked at more than one step during in vivo infection; lower numbers of bacteria reach the Peyer's patches and mesenteric lymph nodes. The spleen and liver are both infected with about equal numbers of bacteria but they do not appear to grow to an equal extent and are more quickly eliminated from the liver. This is a rather surprising finding: we have carried out course of infection experiments with many other attenuated mutants but have never before observed this phenotype. It suggests that the mutant might be unusually susceptible to a specific factor(s) found within the liver. We hypothesize that the difference is due to survival within a specific macrophage population, in this case the Kupffer cell. Additional experiments have shown that the slyA mutant can survive in certain macrophages but essentially not in others (data not shown). Although we have no direct evidence for the precise role that salmolysin plays in macrophage survival, our hypothesis is that this difference in survival in diverse macrophages populations lies at the level of expression of slyA. If this is true, it would suggest that Salmonella is somehow able to distinguish certain differentiated macrophages and that salmolysin is critical for survival within these macrophages. The fact that slyA is found in Salmonella, Shigella, and EIEC suggests that these bacteria may share a similar virulence mechanism, perhaps related to survival within macrophages. All three organisms can cause an inflammatory diarrhea. Salmonella more often causes a disseminated infection, while Shigella and EIEC remain within the colonic epithelium, rarely spreading past the lamina propria to produce a disseminated infection. We believe that salmolysin plays crucial part in this process by defending the bacteria against the early onslaught of phagocytic cells.

ACKNOWLEDGMENTS

We are grateful to Virginia Miller for probing blots of Enterobacteriacea with the salmolysin gene. We are grateful Kim Barrett for assistane with the transcytosis experiments and Annette Wunderlich and Jeff Lipps for assistance with the animal studies and Susie Muir with the mapping studies. The work was supported by NIH grant AI-22933 (F.H.), program project grant AM-35-108, and training grant 5 T32 AI07036.

LITERATURE CITED

1. Mims, S. A. (1982) *The Pathogenesis of Infectious Diesease*. (Academic Press).
2. Welch, R. A. (1991) *Mol. Micro.* 5, 521–528.
3. Braun, V. & Focareta, T. (1991). *Critical Reviews in Microbiology*. 18, 115–158
4. Welch, R. A., Dellinger, E. P., Minshew, B., & Falkow, S. (1981) *Nature*. 294, 665–667.
5. Bhakdi, S., Mackman, N., & Holland, I. B. (1986) *Infect. Immun.* 52, 63–69.
6. Bhakdi, S., Muhly, M., Korom, S., & Schmidt, G. (1990) *J. Clin. Inv.* 85, 1746–1753.
7. Cavalieri, S. J. & Snyder, I. S. (1984) *Infect. Immun.* 37, 966–974.
8. Konig, B., Konig, W., Scheffer, J., Hacke, R., & Goebel, W. (1986) *Infect. Immun.* 54, 886–892.
9. Moulder, J. W. (1991) *Micro. Revi.* 55, 143–190.
10. Turco, J. & Winkler, H. (1991) *Infect. Immun.* 59, 1647–1655.
11. Finlay, B. B. & Falkow, S. (1989) *Micro. Rev.* 53, 210–230
12. Andrews, N. W., Abrams, C. K., Slatin, S. L., & Giffiths, G. (1990) *Cell.* 61, 1277–1287.
13. Gaillard, J. L., Berche, P., Mounier, J., Richard, S., & Sansonetti, P.(1987) *Infect. Immun.* 55, 1641–1646.
14. Kathariou, S., Metz, P., Hof, H., & Goebel, W., (1987) *J. Bact.* 169, 1291–1297.
15. Portnoy, D., Jacks, P. S., & Hinrichs, D. J. (1989) *Infect. Immun.* 57, 477–486.
16. Hage-Chahine, C. M., Giudice, G. D., Lambert, P. H., & Pechere, J. C. (1992) *Infect. Immun.* 60, 1415–1421.
17. Bielecki, J., Youngman, P., Connelly, P., & Portnoy, D. A. (1990) *Nature.* 345, 175–176
18. Friedman, A. M., Long, S. R., Brown, S. E., Bukema, W. J., & Ausubel, F. M. (1982) *Gene*. 18, 289–296.
19. Sambrook, J., Fritsch, E. F., & Maniatis, T. (1989) *Molecular Cloning. A Laboratory Manual* 2nd ed. (Cold Spring Harbor: Cold Spring Harbor Laboratory Press).
20. Benson, N. R. & Goldman, B. S. (1992) *J. Bact.* 175, 1673–1681.
21. Roberts, R. C., Burioni, R., & Helinski, D. R. (1990) *J Bact.* 172, 6204–6216.
22. Simon, R., Priefer, U., & Puhler, A. (1983) *Molecular Genetics of Plant-Microbe iInteractions*. ed. A. Puhler. (St. Paul, Minn.: APS Press) pp. 98–106.
23. Rosenberg, A. H., Lade, B. N., Chui, D. S., Lin, S. W., Dunn, J. J., & Studier, F. W. (1987) *Gene.* 56, 125–136.
24. Studier, F. W., Rosenberg, A. H., Dunn, J. J., & Duberndorff, J. W. (1990) *Methods in Enzymology*. (Academic Press, San Diego) Vol. 185 pp.6–89
25. Neu, H. C. & Hepple, L. A. (1965) *J. Biol Chem.* 240, 3685–3692

26. Songer, J. G., Libby, S. J., Iandolo, J. J., & Cuevas, W. (1990) *Infect. Immun.* 58, 131–136.
27. Buchmeier, N. A. & Heffron, F. (1989) *Infect. Immun.* 57, 1–7.
28. Youderian, P., Sugiono, P., Brewer, K. L., Higgins, P., & Elliot, T. (1988) *Genetics.* 118, 581–592.
29. Neidhardt, F. C., (1987) ed. *Escherichia coli* and *Salmonella typhimurium. Cellular and Molecular biology.* (American Society of Microbiology. Washington, D.C.)
30. Rennie, R. P., Freer, J. J., & Arbuthnott, J. P. (1974) *J. Med. Micro.* 7, 189–195
31. Buchmeier, N. & Heffron, F. (1991) *Infect Immun.* 59, 2232–2238
32. Buchmeier, N. & Heffron, F. (1990) *Science.* 248, 730–732.
33. Groisman, E. A., Chiao, E., Lipps, C. J., & Heffron, F. (1989) *Proc Nat Acad Sci.* 86, 7077–7082.
34. Fields, P. I., Groisman, E. A., & Heffron, F. (1989) *Science.* 243, 1059–1062.
35. Fields, P. I., Swanson, R. V., Haidaris, C. G., & Heffron, F. (1986) *Proc Nat Acad Sci.* 83, 5189–5193.
36. Fang, F. C., Libby, S. J., Buchmeier, N., Loewen, P., Switala, J., & Guiney, D. (1992) *Proc. Natl. Acad. Sci.* in Press.
37. Mulvey, M. R., Switala, J., Andrew, B., & Loewen, P. C. (1990) *J. Bact.* 172, 6713–6720

---

What is claimed is:

1. An isolated slyA salmolysin having an amino acid sequence according to SEQ ID NO:2.

2. An isolated DNA coding a slyA salmolysin having a DNA sequence according to SEQ ID NO:1.

3. An isolated oligonucleotide having a sequence according to SEQ ID NO:3, SEQ ID NO:4, or SEQ ID NO:5.

4. A vector comprising the DNA of claim 2.

5. An expression vector comprising the DNA of claim 2.

6. A transformed microorganism comprising the vector of claim 5.

* * * * *

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
        ( A ) LENGTH: 720 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: SALMONELLA ( x i ) SEQUENCE DESCRIPTION: SEQ ID NO:1:

```
ATCGATGCTT  TAGTTTTAGC  CAAAACTGAA  GCTACAGGTG  CCAAGTGCGC  ACTATGTCTG    60
AAAAAATGTC  TATTGGTAAG  CAAATTTAGC  AATACATTTG  TTTTGAGAAT  ACAAATACTG   120
CACACTATTC  TAAAATCAGC  ATAATAACTT  AGCAAGCTAA  TTATAAGGAG  ATGAAATTGG   180
AATCGCCACT  AGGTTCTGAT  CTGGCACGGT  TGGTGCGCAT  TTGGCGTGCT  CTGATTGACC   240
ATCGCCTCAA  GCCTCTGGAA  TTGACGCAGA  CACATTGGGT  CACGTTGCAC  AATATTCATC   300
AATTGCCGCC  TGACCAGTCG  CAGATTCAAT  TGGCTAAAGC  GATAGGCATT  GAGCAGCCAT   360
CGCTGGTACG  CACGTTGGAT  CAACTTGAAG  ATAAGGGGCT  AATTTCGCGG  CAAACCTGCG   420
CCAGCGATCG  TCGCGCTAAG  CGGATTAAAC  TGACCGAAAA  AGCGGAGCCG  CTGATCGCTG   480
AGATGGAAGA  GGTCATTCAT  AAAACGCGCG  GTGAAATTTT  GGCTGGGATT  TCTTCAGAGG   540
AGATTGAGCT  TCTGATTAAA  CTTATCGCCA  AACTTGAACA  CAATATTATG  GAATTGCACT   600
CTCACGATTG  AGGTGCAGGG  GCATACGTGT  GGCCATGTGA  CCACGTAA   AGCCTGGTTT   660
AGCGTGGAGA  GACGGTAACC  TGGCTGCCGT  TGCTGGCCAG  CACGACACGC  TGACCTGCCG   720
```

( 2 ) INFORMATION FOR SEQ ID NO:2:

( i ) SEQUENCE CHARACTERISTICS:
        ( A ) LENGTH: 146 amino acids
        ( B ) TYPE: amino acid
        ( D ) TOPOLOGY: linear ( i i ) MOLECULE TYPE: protein ( i i i ) HYPOTHETICAL: NO ( i v ) ANTI-SENSE: NO ( v i ) ORIGINAL SOURCE:
    ( A ) ORGANISM: SALMONELLA ( x i ) SEQUENCE DESCRIPTION: SEQ ID NO:2:

```
Met Lys Leu Glu Ser Pro Leu Gly Ser Asp Leu Ala Arg Leu Val Arg
 1               5                  10                  15
Ile Trp Arg Ala Leu Ile Asp His Arg Leu Lys Pro Leu Glu Leu Thr
                20                  25                  30
Gln Thr His Trp Val Thr Leu His Asn Ile His Gln Leu Pro Pro Asp
             35                  40                  45
Gln Ser Gln Ile Gln Leu Ala Lys Ala Ile Gly Ile Glu Gln Pro Ser
         50              55                  60
Leu Val Arg Thr Leu Asp Gln Leu Glu Asp Lys Gly Leu Ile Ser Arg
 65                  70              75                      80
Gln Thr Cys Ala Ser Asp Arg Arg Ala Lys Arg Ile Lys Leu Thr Glu
                 85             90                      95
Lys Ala Glu Pro Leu Ile Ala Glu Met Glu Glu Val Ile His Lys Thr
                100             105                 110
Arg Gly Phe Ile Leu Ala Gly Ile Ser Ser Glu Glu Ile Phe Leu Leu
             115             120                 125
Ile Lys Leu Ile Ala Lys Leu Glu His Asn Ile Met Glu Leu His Ser
         130             135                 140
His Asp
145
```

( 2 ) INFORMATION FOR SEQ ID NO:3:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: DNA (genomic)

( v i ) ORIGINAL SOURCE:
        ( A ) ORGANISM: SALMONELLA ( x i ) SEQUENCE DESCRIPTION: SEQ ID NO:3:

ATCGATGCTT TAGTTTTAGC CAA                                              23

( 2 ) INFORMATION FOR SEQ ID NO:4:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE: DNA (genomic)

( v i ) ORIGINAL SOURCE:
        ( A ) ORGANISM: SALMONELLA ( x i ) SEQUENCE DESCRIPTION: SEQ ID NO:4:

ATTATAAGGA GATGAAATTG GAATCGCC                                    28

( 2 ) INFORMATION FOR SEQ ID NO:5:

( i ) SEQUENCE CHARACTERISTICS:
        ( A ) LENGTH: 26 base pairs
        ( B ) TYPE: nucleic acid
        ( C ) STRANDEDNESS: single -continued (D) TOPOLOGY: linear ( i i ) MOLECULE TYPE: DNA (genomic)

( v i ) ORIGINAL SOURCE:
 (A) ORGANISM: SALMONELLA ( x i ) SEQUENCE DESCRIPTION: SEQ ID NO:5:

CGGTCCAATG GCAGAGAGGT GCGATT 26